United States Patent
Littman et al.

[11] 4,097,560
[45] Jun. 27, 1978

[54] NOVEL PHOSPHORUS COMPOUNDS AND FLAME RETARDANT COMPOSITIONS CONTAINING SAME

[75] Inventors: Stanley Littman, Sharon, Mass.; Irving Touval, Edison, N.J.

[73] Assignee: M & T Chemicals Inc., Stamford, Conn.

[21] Appl. No.: 811,050

[22] Filed: Jun. 29, 1977

[51] Int. Cl.² ............... C07F 9/28; C08K 5/53
[52] U.S. Cl. ............... 260/931; 8/116 P; 106/15 FP; 260/2 P; 260/2.5 AJ; 260/45.7 P; 260/865; 260/969; 427/390 D; 428/276
[58] Field of Search ............... 260/2 P, 2.5 AJ, 931, 260/45.7 P, 969; 428/276; 106/15 FP

[56] References Cited
U.S. PATENT DOCUMENTS

| | | | |
|---|---|---|---|
| 3,483,279 | 12/1969 | Davis et al. | 260/969 |
| 3,730,917 | 5/1973 | Hesskamp | 260/2.5 AJ |
| 3,836,507 | 9/1974 | Yoshizawa et al. | 260/45.7 P |
| 4,044,076 | 8/1977 | Kametani et al. | 260/931 |

*Primary Examiner*—Melvyn I. Marquis
*Assistant Examiner*—R. A. White
*Attorney, Agent, or Firm*—Kenneth G. Wheeless; Robert Spector

[57] ABSTRACT

Novel phosphorus compounds of the general formula

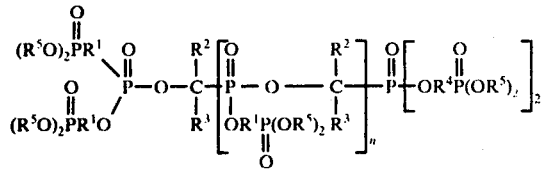

contain up to 22% or more of phosphorus and impart an effective level of flame retardancy to a variety of natural and synthetic materials.

22 Claims, No Drawings

NOVEL PHOSPHORUS COMPOUNDS AND FLAME RETARDANT COMPOSITIONS CONTAINING SAME

BACKGROUND OF THE INVENTION

This invention relates to a class of novel phosphorus compounds. This invention further relates to a method for imparting flame retardancy to natural and synthetic materials using a class of novel phosphorus compounds containing high concentrations of phosphorus and exhibiting unique properties which make them particularly desirable as flame retarding agents and intumescent coatings.

Since the early nineteenth century phosphorus compounds have been used to impart flame retardancy to natural and synthetic materials. A large number of phosphorus compounds that have been used for this purpose are discussed in chapter 2 of a text entitled "The Chemistry and Uses of Fire Retardants" by John W. Lyons (John Wiley and Sons, 1970).

Esters of the various phosphorus-containing acids, particularly phosphates, phosphites, phosphonates, phosphonites, phosphinates and phosphinites are among the most widely used phosphorus-containing flame retardants, as are tertiary phosphines and phosphine oxides.

Triesters of phosphoric acid such as triethyl phosphate contain relatively high concentrations of phosphorus, however these compounds are volatile and decompose at relatively low temperatures, particularly in the presence of water. The volatility and water solubility of tertiary alkyl phosphates can be decreased with a corresponding decrease in phosphorus content by employing higher molecular weight alcohols and phenols as the esterifying reagent. An example of such a compound is tricresyl phosphate.

In addition, tertiary phosphates function as plasticizers for many synthetic polymers, and would adversely affect the physical properties of the polymer when employed in the amount required to achieve the desired phosphorus content. Tertiary phosphates containing one or more halogen atoms in the molecule have been found to improve flame retardancy while decreasing the volatility and water solubility of the ester, however this advantage may be more than offset by the inherently poor light stability of halogen compounds. The resultant decomposition products could discolor a polymer containing these flame retardants. The compounds therefore would not be useful if long term color retention was a criterion for an acceptable flame retarded product. This would also be true for other halogen-containing phosphorus compounds.

Esters of other phosphorus-containing acids such as phosphonous, phosphonic and phosphinic acids exhibit many of the undesirable properties disclosed hereinabove for the tertiary phosphates. The prior art discloses classes of phosphorus compounds which avoid these shortcomings. One way of reducing the tendency of the phosphorus compound to decompose, volatilize or be leached out of the substrate is to provide it with two or more functional groups or a carbon-carbon double bond for the purpose of copolymerizing the compound with one or more additional monomers to form an inherently flame retardant material. This approach has been widely used for preparing polyesters and polyurethanes.

A second method for achieving improved performance for the flame retarding agent in the substrate has been to prepare compounds of relatively high molecular weight containing a plurality of phosphorus atoms. An example of such a compound is the oligomeric chloroalkyl phosphonate represented by the formula

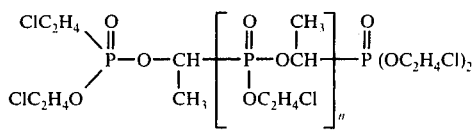

where $n$ is an integer greater than 1.

Compounds of this type are disclosed in U.S. Pat. No. 3,014,956. These oligomers would be less likely to vaporize or decompose than the simple esters of phosphorus-containing acids, however the chlorine present in these materials could adversely affect the light stability of the final formulation. In addition, at elevated temperatures oligomers would have a tendency to decompose and discolor in a manner similar to halogen-containing polymers such as polyvinyl chloride. It would therefore be necessary to include stabilizers if polymer compositions containing these flame retardants are exposed to light or elevated temperatures for extended periods of time.

At combustion temperatures most, if not all, of the phosphorus compounds disclosed in the preceding paragraphs decompose exothermically. The amount of heat generated upon decomposition of these compounds would raise the flame temperature and thereby reduce the flame-retarding effect of the phosphorus compound.

One objective of this invention is to define a class of compounds containing a high concentration of phosphorus, preferably 20% by weight or more. A second objective of this invention is to increase the flame retardancy imparted to natural and synthetic materials by prior art phosphorus compounds.

It has now been found that a particular class of phosphorus compounds containing as much as 22% or more by weight of phosphorus is unique in that preferred members of this class decompose endothermically, thereby withdrawing heat during combustion of the substrate.

SUMMARY OF THE INVENTION

This invention provides a novel class of phosphorus compounds containing up to 22% and more by weight of phosphorus, wherein said class of compounds exhibit the general formula

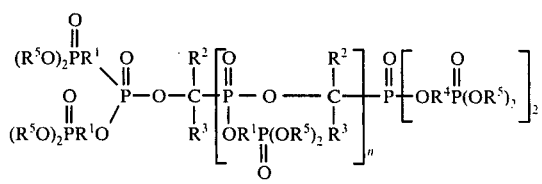

wherein $R^1$ and $R^4$ are each the same or different alkylene and contain from 1 to 12 carbon atoms, $R^2$ and $R^3$ are individually selected from the group consisting of hydrogen and alkyl containing from 1 to 12 carbon atoms, $R^5$ is alkyl and contains from 1 to 12 carbon atoms and $n$ represents an integer having an average value of from 1 to about 50.

DETAILED DESCRIPTION OF THE INVENTION

The present phosphorus compounds are unique by virtue of a combination of high phosphorus content, low volatility and, in the preferred embodiments, an endothermic decomposition accompanied by intumescence, which increases the efficacy of these compounds as flame retarding agents.

The novel compounds of this invention can be prepared by reacting a tertiary alkyl phosphite with an oligomeric reaction product of a bis(haloalkyl) phosphorohalidite, an aldehyde or ketone and a trivalent phosphorus ester. These oligomeric reaction products are known in the art, and are described in U.S. Pat. No. 3,014,956, the pertinent sections of which are hereby incorporated by reference. A preferred intermediate is the oligomeric reaction product of tris($\beta$-chloroethyl) phosphite, bis(2-chloroethyl) phosphorochloridite and acetaldehyde. Oligomers containing an average of $n$ repeating units are formed when $n$ moles of carbonyl compound and $n$ moles of bis(haloalkyl) phosphorohalidite are employed for each mole of trivalent phosphorus ester, $n$ being an integer greater than 1. General equations for formation of the intermediate obtained using a tris-haloalkyl phosphite are believed to be $$(XR^1O)_2PX + R^2R^3C=O + P(OR^4X)_3 \longrightarrow$$

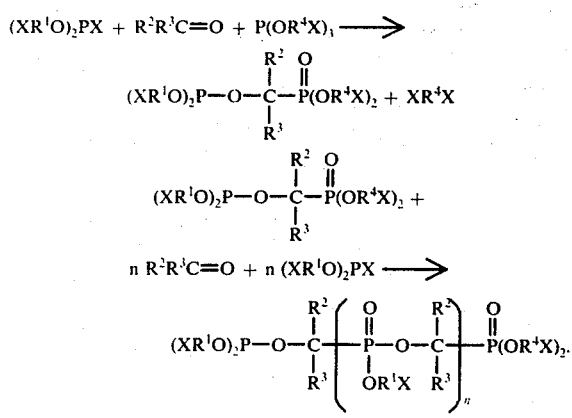

Upon heating at temperatures of from 135° to 225° C. the terminal $(XR^1O)_2P$—O— group is converted to

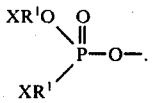

This reaction is reported in the aforementioned U.S. Pat. No. 3,014,956.

In the foregoing equations X is halogen, $R^2$ and $R^3$ are individually selected from hydrogen and hydrocarbyl groups containing from 1 to about 12 carbon atoms. Preferably the hydrocarbyl group is lower alkyl due to availability of the carbonyl compounds. $R^1$ and $R^4$ represent identical or different alkylene groups containing from 1 to 12 carbon atoms. Preferably $R^1$ and $R^4$ are both ethylene. This preference is based on the availability of the 2-haloethylphosphites and the corresponding bis(2-haloethylphosphonohalidites). Both of these compounds are conveniently prepared by reacting ethylene oxide with a phosphorus trihalide using 2 or 3 moles of ethylene oxide for each mole of the phosphorus trihalide.

The compounds of this invention are prepared by reacting one or more of the oligomeric halogen-containing phosphonates described in the preceding paragraphs with a quantity of trialkyl phosphite sufficient to react with all of the halogen atoms present in the phosphonate. The reaction of tertiary phosphites with halogen-containing organic compounds is known as the Michaels-Arbuzov reaction and can be represented by the following equation.

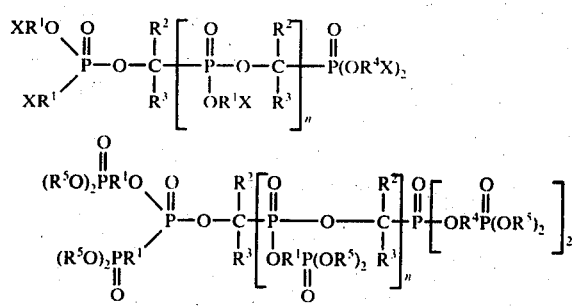

Preferred embodiments of the present compounds contain about 22% by weight of phosphorus, are relatively non-volatile, and contain no halogen that would tend to decompose and discolor the compound. This combination of properties would suffice to make the present compounds desirable flame retarding agents. An additional and unexpected property of the present compounds is that the decomposition of these compounds at elevated temperatures is an endothertic reaction, in that heat is absorbed from the environment. This is considered surprising since both of the starting materials (the tertiary phosphite and the halogen-containing oligomeric phosphonate) decompose exothermically with considerable evolution of heat. This is undesirable for a flame retarding agent, since it would increase the temperature of the flame. This at least partially offsets the beneficial effect of the flame retarding agent.

Preferred embodiments of the present compounds intumesce during decomposition, thereby forming an insulating layer between the flame and the substrate.

Materials which can be effectively flame retarded using the novel compounds of this invention include both natural and synthetic polymers in the form of coatings, fibers, fabrics and films, in addition to shaped articles having 3 major dimensions that can be formed by molding, casting and other well-known techniques. The present compounds can either be blended together with the polymer prior to shaping or can be applied to the surface of a finished article such as a cotton fabric. Among the natural materials which can be treated with the present compounds are cotton, wood, paper, cardboard, pressed board, wool, rayon and the various cellulose derivatives, including cellulose esters such as cellulose acetate and cellulose ethers such as methyl cellulose and carboxymethyl cellulose.

The present compounds impart useful levels of flame retardancy to most classes of synthetic polymers. These polymers are formed by addition or condensation type reactions involving molecules capable of reacting with two or more other molecules to form linear or cross-linked structures having molecular weights of 1,000 or more. Among the major classes of synthetic organic polymers formed by addition polymerization are polyolefins such as polyethylene, vinyl polymers such as polyvinyl chloride and styrene, acrylic polymers such as poly(methyl methacrylate) and polyacrylonitrile and the class of synthetic rubbers formed by polymerization of neoprene or chloroprene. Condensation polymers include polyesters (both saturated and unsaturated types), polyamides, polyimides, polyurethanes (both cellular and non-cellular), epoxy resins, resins obtained by reacting aldehydes, particularly formaldehyde, with phenols or amines, particularly the amino substituted triazine referred to as "melamine".

The amount of flame retarding agent required to impart an effective level of flame retardancy to a given substrate is determined by a number of factors, including the composition and thickness of the substrate. Usually from 0.5 to 20% of one of the present phosphorus compounds will suffice to provide the desired level of flame retardancy.

The following examples disclose preferred embodiments of this invention and should not be interpretted as limiting the scope of the accompanying claims. All parts and percentages are by weight unless otherwise specified.

EXAMPLE 1

This example describes the preparation of a preferred compound of this invention. A three liter-capacity reactor was equipped with a mechanically driven stirrer, thermometer and a water-cooled reflux condenser, the outlet side of which was connected to a receiver immersed in a solid carbon dioxide-acetone bath for the purpose of recovering the ethyl chloride generated as a by-product of this reaction. The reactor was charged with 2500 g. (15 moles) of triethyl phosphite and 1600 g. of an oligomeric reaction product of the general formula

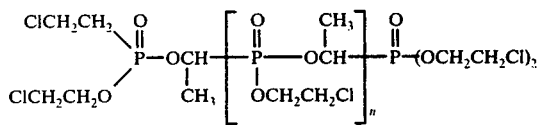

wherein the average value of $n$ is 3.7.

The contents of the reactor were heated to the boiling point (154° C.), at which time the evolution of ethyl chloride was noted. The ethyl chloride was isolated and collected in the receiver by maintaining the temperature of the water circulating in the reflux condenser at between 30° and 35° C. This temperature was sufficiently low to condense the vaporized ethyl phosphite and return it to the reactor.

Heating of the reaction mixture was continued for 48 hours, during which time the boiling point of the reaction mixture increased to 180° C., at which point no condensation of liquid was observed in the reflux condenser. A total of 840 g. of ethyl chloride was collected during this period. The contents of the reactor were then distilled under reduced pressure (24 mm. Hg) at a temperature of 180° C. to remove unreacted triethyl phosphite. The liquid residue in the reactor was colorless, transparent and weighed 2507 g. The residue was found to contain 22.5% phosphorus and no chlorine. The oligomeric phosphinate employed as one of the starting materials for the reaction contains 15% phosphorus and 19% chlorine. These analytical data indicate that substantially all of the oligomeric phosphonate had reacted with the triethyl phosphite.

EXAMPLE 2

This example describes the preparation of a second preferred compound of this invention.

The synthetic procedure described in the preceding Example 1 was repeated using a different oligomeric phosphate-phosphonate. The oligomer was prepared using the same reagents as the one described in Example 1, however the ratio of acetaldehyde and bis(2-chloroethyl) phosphorochloridite to tris(2-chloroethyl) phosphite was adjusted such that the average value of $n$ in the formula of Example 1 was 22. The liquid residue remaining following removal of the unreacted triethyl phosphite was clear, colorless and was found to contain 22.2% phosphorus and no chlorine. As in Example 1, the higher phosphorus content and absence of chlorine indicates that the oligomer had reacted with the triethyl phosphite to form one of the novel compounds of this invention.

EXAMPLE 3

A differential thermal analysis was performed using the product of the foregoing Example 2. The resultant plot of $\Delta T$ against sample temperature was compared with the plot obtained using the oligomeric phosphonate employed as one of the starting materials to prepare the compound. The plot for the reaction product exhibited a significant endotherm ($\Delta T = -1.25$) beginning at 240° C. The plot of the oligomeric starting material exhibited an exotherm ($\Delta T = +1.75°$ C.) beginning at about 150° C.

The reaction product of Example 2 converted to a white foam when heated above about 275° C. This property of intumescence is advantageous for a flame retarding agent, since it would form a thermal barrier between the flame and the substrate. This barrier protects the substrate from further degradation, thereby reducing fuel formation. The intumescent layer also excludes air from the base of the flame.

EXAMPLE 4

This example demonstrates the high level of flame retardancy imparted to a polyester fiber using a preferred phosphorus compound of this invention.

An undrawn, untwisted, semi-dull yarn of 550 denier containing 35 polyethylene terephthalate filaments was drawn while immersed in a solution containing 200 g. of the reaction product described in the foregoing Example 2 for every one liter of the monobutyl ether of ethylene glycol. The draw ratio, i.e. the ratio of the circumferential speeds of the draw and feed rolls was 3.6 and the draw bath was at ambient temperature. The residence time of the fiber in the drawing medium was about 0.5 second. The drawn yarn was passed through a methanol bath to remove excess drawing medium after which it was wound on a U-shaped frame and scoured using perchloroethylene. The scoured yarn was then laundered by being placed in a container of commercial laundry detergent (25 g.) and warm water (0.95 liter). The container was then shaken for 1.5 hours. The yarn was then analyzed for phosphorus and was found to contain 1.6% of this element, equivalent to 7.3% of the compound.

A second sample of the same polyethylene terephthalate yarn was drawn as described in the preceding paragraph using a draw bath which contained only the monobutyl ether of ethylene glycol.

The limiting oxygen index value of the two yarn samples was determined by placing the U-shaped frames containing the yarn samples in a vertically oriented Pyrex ® glass tube. Known mixtures of oxygen and nitrogen were introduced at the base of the tube and a flame was applied to the upper end of each frame. The limiting oxygen index (L.O.I.) value was calculated using the formula $$\text{L.O.I.} = \frac{[O_2]}{[O_2] + [N_2]} \times 100$$

wherein $[O_2]$ represents the minimum flow rate of oxygen that will support combustion and $[N_2]$ is the flow rate for nitrogen, expressed in any convenient units such as cc./minute.

The L.O.I. value for the yarn sample containing the phosphorus compound of Example 2 was 28.5. The value for the control was 21.0. L.O.I. values of 21 or less indicate that the material will burn in air.

EXAMPLE 5

This example demonstrates the high level of flame retardancy imparted to a cotton fabric by one of the preferred phosphorus compounds of this invention.

A sample of cotton muslin was dipped into a solution containing 20 g. of the phosphorus compound described in the preceding Example 2 per liter of the monobutyl ether of ethylene glycol. The fabric was then passed between a pair of nip rollers and dried at a temperature of 60° C. The dried fabric was subjected to the Children's Sleepwear Test (Department of Commerce test PFF-5-73, published in the Federal Register, volume 38, number 47, pages 6700-6710). The burn length of the sample was less than two inches (5 cm.), and the flame went out upon removal of the sample from the burner flame employed to ignite the sample.

EXAMPLE 6

This example demonstrates that useful levels of flame retardancy can be imparted to polyurethane foams using the compounds of this invention.

A flexible urethane foam was prepared by combining the following ingredients:

| | |
|---|---|
| Glycerin-based polypropylene glycol, hydroxyl no. = 65. | 100 parts |
| Commercial tolylene diisocyanate | 45 parts |
| Deionized water | 3.5 parts |
| A poly(oxyalkylene) siloxane | 1.0 part |
| N-ethyl morpholine | 0.3 part |
| Triethylene diamine (as a 33% solution in dipropylene glycol) | 0.3 part |
| 1:1 weight ratio mixture of stannous octoate and dioctyl phthalate | 0.6 part |
| Flame retardant | as indicated |

The following table summarizes the limiting oxygen index (L.O.I.) values for polyurethane foams containing (a) 10 parts of the phosphorus compound prepared as described in Example 1; (b) 10 parts of the halogen-containing oligomeric phosphonate employed as one of the starting materials to prepare the product of Example 1 and (c) no flame retardant.

| Flame Retardant | L.O.I. Value |
|---|---|
| Product of Example 1 | 26.9 |
| Starting material of Example 1 | 22.9 |
| None | 16.0 |

These data demonstrate that the foam sample containing one of the present compounds exhibited a considerably higher level of flame retardancy than a foam containing an equal weight of the starting material employed to prepare the present compound. The starting material is a commercially available flame retardant.

What is claimed is:

1. A novel phosphorus compound of the general formula

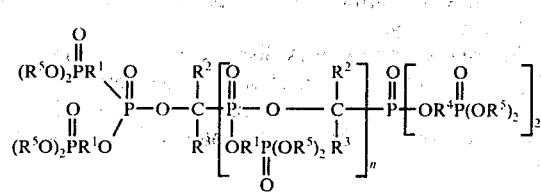

wherein $R^1$ and $R^4$ are each the same or different alkylene and contain from 1 to 12 carbon atoms, $R^2$ and $R^3$ are individually selected from the group consisting of hydrogen and alkyl containing from 1 to 12 carbon atoms, $R^5$ is alkyl and contains from 1 to 12 carbon atoms and $n$ represents an integer having an average value of from 1 to about 50.

2. A novel phosphorus compound according to claim 1 wherein $R^1$ and $R^4$ each contain from 1 to 4 carbon atoms.

3. A novel phosphorus compound according to claim 2 wherein $R^1$ and $R^4$ are ethylene.

4. A novel phosphorus compound according to claim 1 wherein $R^2$ is hydrogen and $R^3$ is alkyl and contains from 1 to 4 carbon atoms.

5. A novel phosphorus compound according to claim 4 wherein $R^3$ is methyl.

6. A novel phosphorus compound according to claim 1 wherein the average value represented by $n$ is from 3 to 22.

7. A novel phosphorus compound according to claim 1 wherein $R^5$ contains from 1 to 4 carbon atoms.

8. A novel phosphorus compound according to claim 7 wherein $R^5$ is ethyl.

9. A flame retardant composition consisting essentially of (1) a substrate that, in turn, consists essentially of a natural or synthetic organic polymer, and (2) a flame retarding agent of the general formula

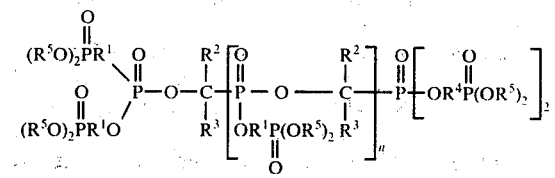

wherein $R^1$ and $R^4$ are each the same or different alkylene and contain from 1 to 12 carbon atoms, $R^2$ and $R^3$ are individually selected from the group consisting of hydrogen and alkyl containing from 1 to 12 carbon atoms, $R^5$ is alkyl and contains from 1 to 12 carbon atoms and $n$ represents an integer having an average value of from 1 to about 50, wherein the amount of said flame retarding agent is sufficient to impart the desired level of flame retardancy to said substrate.

10. A flame retardant composition according to claim 9 wherein the concentration of flame retarding agent is from 0.5 to 20%, based on the weight of said composition.

11. A flame retardant composition according to claim 9 wherein $R^1$ and $R^4$ each contain from 1 to 4 carbon atoms.

12. A flame retardant composition according to claim 11 wherein $R^1$ and $R^4$ are ethylene.

13. A flame retardant composition according to claim 9 wherein $R^2$ is hydrogen and $R^3$ is alkyl and contains from 1 to 4 carbon atoms.

14. A flame retardant composition according to claim 13 wherein $R^3$ is methyl.

15. A flame retardant composition according to claim 9 wherein the average value represented by $n$ is from 3 to 22.

16. A flame retardant composition according to claim 9 wherein $R^5$ contains from 1 to 4 carbon atoms.

17. A flame retardant composition according to claim 16 wherein $R^5$ is ethyl.

18. A flame retardant composition according to claim 9 wherein said substrate consists essentially of a synthetic organic polymer.

19. A flame retardant composition according to claim 18 wherein said synthetic organic polymer is selected from the group consisting of polyesters and vinyl polymers.

20. A flame retardant composition according to claim 9 wherein said substrate consists essentially of cotton fibers.

21. A flame retardant composition according to claim 9 wherein said flame retarding agent is evenly distributed throughout the substrate.

22. A flame retardant composition according to claim 9 wherein said flame retarding agent is present only on the surfaces of the substrate.

* * * * *